Nov. 20, 1945. W. E. LAMMERTS Plant Pat. 661
PEACH TREE
Filed Jan. 17, 1945
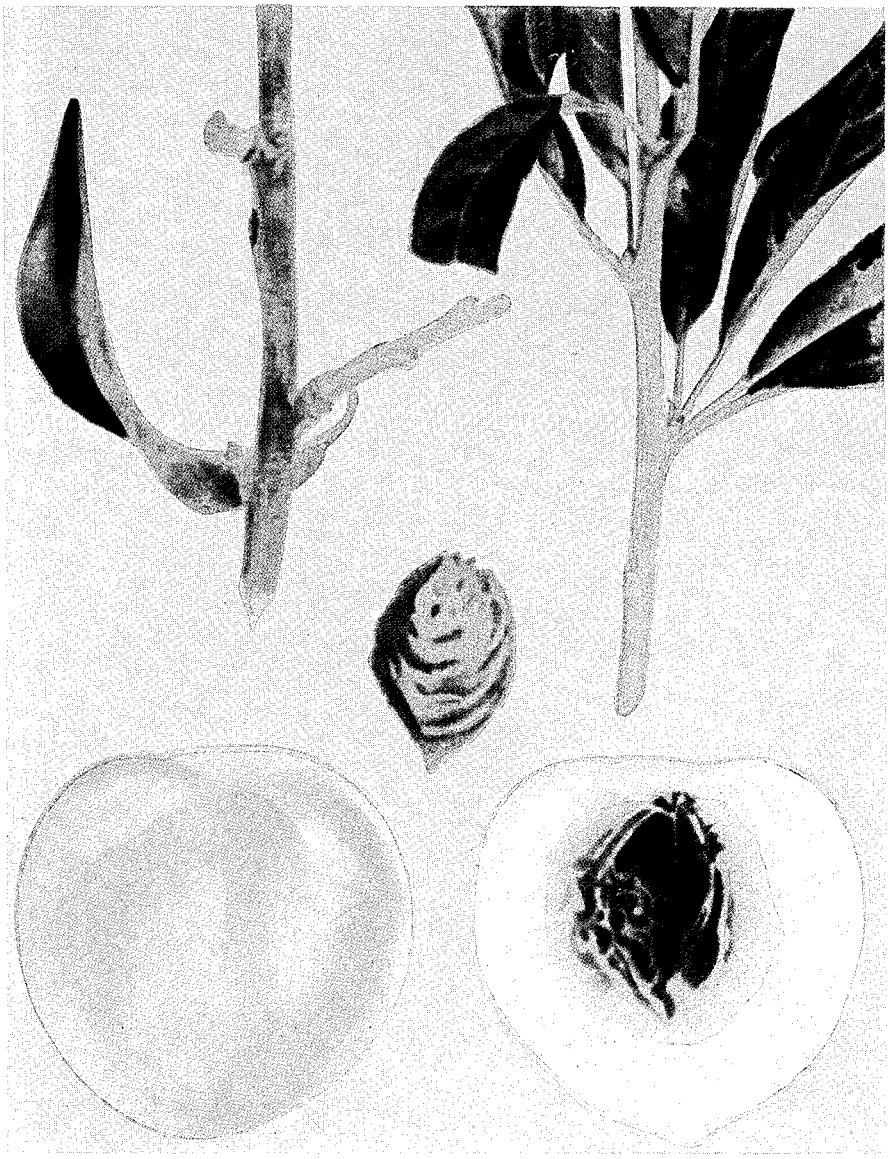
Inventor
W E Lammerts
By Robb & Robb
His Attorneys Patented Nov. 20, 1945

Plant Pat. 661

UNITED STATES PATENT OFFICE

661

PEACH TREE

Walter E. Lammerts, West Los Angeles, Calif., assignor to Armstrong Nurseries, Inc., Ontario, Calif., a corporation of California Application January 17, 1945, Serial No. 573,263

1 Claim. (Cl. 47—62)

The present discovery relates to a new and distinct variety of peach tree, which originated from germinating seed resulting from open-pollination of flowers of the "Rio Oso Gem" peach (Plant Patent No. 84).

While this latter peach possesses many excellent qualities when grown in certain districts of California, the distinctions of this new variety from "Rio Oso Gem" are important and will now be more fully set forth.

This new peach presents a combination of characters highly resembling those of "Rio Oso Gem" with, however, a winter chilling requirement very much less than this latter variety but very similar to those of the well known variety "Socala." This makes this new variety very much better suited to planting in Southern California areas of mild winter climate than is "Rio Oso Gem," since there is present in this peach variety the ability to produce a crop each year when winter temperatures are insufficient to satisfy the chilling requirements of "Rio Oso Gem."

Another point of distinction is found in the ripening season, in view of the fact that this new peach is from five to ten days earlier than "Rio Oso Gem," depending upon the season, and more closely approximates the ripening season of "J. H. Hale" peach from which it is distinct in almost every respect except tree habit.

The new variety does resemble "Rio Oso Gem" very much in tree characters, in that it is open-vase formed, upright spreading and medium to small in size.

It may be noted that because of its relatively low chilling requirement as compared with "Rio Oso Gem," it consistently begins to leaf and flower earlier in the season than this latter variety. The leaves of this new peach, measuring on an average of six to seven inches in length, would be classed as "Wavy and crinkled," according to Meader and Blake in American Soc. for Hort. Sci. (203–207—1939, vol. 37) which they place in the arbitrary class 3, as contrasted with leaves of the same length and comparable growth stage of "Rio Oso Gem," classed as "Wavy," class 2, described by these authorities.

Furthermore, leaves of this new variety are considerably thicker and heavier than those of "Rio Oso Gem," being crisp, whereas comparable leaves of "Rio Oso Gem" are limp and flexible. Fruits are somewhat more uniform and smoothly shaped; the stones are distinctly less furrowed and ridged, the ridges being typically more rounded than the ridges of the stones of "Rio Oso Gem" and the amount of pitting is much less than in the latter. These differences in the stone make true the general distinction that the casual appearance of the stones of this new variety is very much smoother than the stone of "Rio Oso Gem."

Other specific points of distinction will appear in the following detailed description of this new peach, color terminology being in accord with Robert F. Wilson Horticultural Colour Chart, except where otherwise indicated.

Asexual reproduction shows that these characteristics hold true through succeeding propagations.

The illustration represents respectively a specimen of a section of a branch, with typical leaf and bud features, a further specimen of foliage with end of crisp leaf broken therefrom, a specimen of stone, and the fruit in elevation for color and form characteristics and in section to show pit cavity characteristics.

Dates of first and last picking—varying somewhat from year to year because of varying winter chill in Southern, California, but usually begin picking August 6th to 10th, ending August 16th to 20th.

Specimens described were grown in Ontario, California.

Tree: Medium to small; medium vigorous; upright spreading; open; vase-formed; very productive; regular bearer.

*Trunk.*—Stocky; medium smooth.

*Branches.*—Stocky to medium; medium smooth; near Snuff Brown (Ridgway) Plate XXIX; Walnut Brown (Ridgway) Plate XXVII, on side exposed to sun; dull. *Lenticels*—few; medium size.

*Leaves.*—Length—4 inches to 7 inches; width—1 inch to 2 inches; size—Medium. Lanceolate; acutely pointed; medium thick; smooth; upper side of mature leaf, near Leaf Green (Ridgway) Plate XLI; under side of mature leaf slightly lighter than Pois Green (Ridgway) Plate XLI; upper side of young leaf near Deep Dull Yellow Green (Ridgway) Plate XXXII; under side of young leaf near Chromium Green (Ridgway) Plate XXXII. *Margin*—glandular before maturity; finely serrate. *Petiole*—short; thick to medium. *Glands*—average number, five to six; opposite and alternate; large to medium; mixed. Glands near or slightly lighter than Chrysolite Green (Ridgway) Plate XXXI, while active. Position—on upper one-half of petiole encroaching on margin of leaf. *Stipules*—medium to short; broad at base; early deciduous.

*Flower-buds.*—Large; long; conic pointed when showing color; plump before showing color; hardiness untested.

*Flowers.*—Dates first and full bloom—ranging from March 3rd to 15th and March 15th to 25th, respectively. Early to medium; large: pink with reddish base.

Fruit: Maturity when described—firm ripe; approximately August 25th.

*Size.*—Large. Diameter axial—2¾ inches to 3¼ inches. Transverse in suture plane—3 inches to 3¼ inches. At right angles to suture plane—2¾ inches to 3¼ inches.

*Form.*—Only slightly variable; slightly asymmetrical; broadly ovoid; compressed laterally toward suture. Fruit is nearly round in cross section at right angles to axial plane. *Suture*—distinct; shallow; extends from base to apex; usually has a very slight marked depression beyond pistil point. *Ventral surface*—slightly lipped throughout left side. Lips—more strongly lipped on left side near base. *Stem cavity*—rounded; slightly elongated in suture plane with suture showing on one side; depth—one-half inch; breadth—⅞ inch; markings—none significant. *Base*—rounded. *Apex*—short; rounded. Pistil point—short; oblique.

*Stem.*—Length—¼ inch to ⅜ inch; stout; glabrous. Adherence to stone—medium strong.

*Skin.*—Medium thickness; tough; tenacious to flesh. Tendency to crack—none in wet or dry season. *Color*—Basic color between and varying from Aureolin, page 3, Plate 3/2, and Empire Yellow, page 66, Plate 603/1. Blushed or overlaid with Delft Rose, page 108, Plate 20/1, and Claret Rose, page 109, Plate 21/1. Portions exposed to sun much darker, close to Spinel Red, page 189, Plate 0023. *Down*—moderate; short; does roll up when rubbed.

*Flesh.*—Near and varying from Lemon Yellow, page 4, Plate 4/2, with flecks and stripes of Turkey Red, page 94, Plate 721, throughout the flesh, but more prominent near the base. *Surface of pit cavity*—Near Crimson, page 22, Plate 22/2, with fibers the same color. *Amygdalin*—moderate. Juice—abundant; rich. *Texture*—firm; fine; crisp to melting. *Fibres*—few; fine; semi-tough. *Ripens*—fairly even; somewhat earliest at apex along lips. *Flavor*—acid; vinous. *Aroma*—pronounced. *Eating quality*—good to best.

Stone: Adheres to flesh slightly along ventral edge.

*Fibres.*—Short.

*Free.*—Parts from flesh smoothly.

*Size.*—Medium. Length—1¼ inches to 1¾ inches; breadth—¾ inch to $1\frac{3}{16}$ inches; thickness—⅝ inch to ¾ inch.

*Forms.*—Obovoid; cuneate toward apex.

*Base.*—Slightly oblique. *Hilum*—narrow; oblong. *Apex*—acuminate.

*Sides.*—Mostly equal; usually slightly curved on left side. *Surface*—irregularly furrowed toward apex; ridged toward apex; pitted from base to above center, but more thickly at base, occasionally some furrowing and ridging near base. Fewer furrows, ridges and pittings than most peach variety stones.

*Ridges.*—Rounded toward base and apex.

*Pits.*—Elongated. *Ventral edge*—medium thickness with wing throughout.

*Dorsal edge.*—Moderately full with shallow, narrow groove toward base to above center. *Ridges*—interrupted.

*Color of Stone.*—Near Mikado Brown (Ridgeway) Plate XXIX; furrows and pits near Nopal Red (Ridgeway) Plate I.

*Tendency to split.*—Slight in wet or dry season.

Use: Market; local; dessert.

Keeping quality: Good.

Resistance to:

*Insects.*—Not significant.

*Diseases.*—Resistance to mildew and brown rot, good.

Shipping quality: Excellent.

I claim:

A new and distinct variety of peach tree, characterized as to novelty by the reduction in winter chilling requirement in comparison with Rio Oso Gem variety under comparable conditions, with resultant ability to produce a crop each year under unfavorable conditions of warm winter temperature; early leafing and flowering season; earlier ripening period compared to its parent variety; distinct form and crispness of leaves; color of the fruit and uniformity and smoothness of fruit and stone, substantially as shown and described.

WALTER E. LAMMERTS.